US010100637B2

(12) United States Patent
Breviere et al.

(10) Patent No.: US 10,100,637 B2
(45) Date of Patent: Oct. 16, 2018

(54) DEVICE FOR AUTOMATICALLY CALIBRATING AN ANALYZER USED FOR MUD GAS OR FLUID LOGGING, ASSOCIATED ANALYSIS SYSTEM AND DRILLING RIG (71) Applicant: Geoservices Equipements SAS, Roissy-en-France (FR)

(72) Inventors: Jerome Breviere, Taverny (FR); Patrick Banik, Aulnay SousBois (FR)

(73) Assignee: GEOSERVICES EQUIPEMENTS, Roissy en France (FR)

( * ) Notice: Subject to any disclaimer, the term of this patent is extended or adjusted under 35 U.S.C. 154(b) by 517 days.

(21) Appl. No.: 14/795,969

(22) Filed: Jul. 10, 2015

(65) Prior Publication Data
US 2016/0010453 A1    Jan. 14, 2016

(30) Foreign Application Priority Data

Jul. 10, 2014 (EP) ..................... 14290204

(51) Int. Cl.
*G01N 33/00* (2006.01)
*E21B 49/08* (2006.01)
*G01N 33/28* (2006.01)
*G01N 30/88* (2006.01)
*G01N 30/04* (2006.01)

(52) U.S. Cl.
CPC ........... *E21B 49/086* (2013.01); *G01N 30/88* (2013.01); *G01N 33/0006* (2013.01); *G01N 33/2823* (2013.01); *G01N 2030/047* (2013.01); *G01N 2030/8854* (2013.01)

(58) Field of Classification Search
CPC .............. G01N 30/88; G01N 30/8854; G01N 2030/047; G01N 33/0006

USPC ....... 73/1.02, 1.03, 1.06, 1.07, 23.22, 23.23; 702/87, 88, 104
See application file for complete search history.

(56) References Cited

U.S. PATENT DOCUMENTS

| 4,635,735 A | | 1/1987 | Crownover |
| 5,329,804 A | * | 7/1994 | Germany ............. A61B 5/1491 73/1.06 |
| 5,804,695 A | * | 9/1998 | Dageforde ......... G01N 33/0031 73/1.07 |

(Continued)

FOREIGN PATENT DOCUMENTS

| EP | 0640833 A1 | 3/1995 |
| FR | 2799790 | 4/2001 |

OTHER PUBLICATIONS

Extended European Search Report for European Application No. 14290204.8 dated Nov. 11, 2014.

*Primary Examiner* — Robert R Raevis
(74) *Attorney, Agent, or Firm* — Michael Dae (57) ABSTRACT A device (118) for automatically calibrating an analyzer (112) used for mud gas or fluid logging, comprising:
a cabinet (140) having a plurality of dedicated reception slots (144), each slot (144) being configured for the insertion of a canister (148) containing a known calibration mixture, the cabinet (140) containing:
a main line (174) to be connected to the analyzer (112),
a connection assembly able to selectively connect each reception slot (144) to the main line (174),
a control unit (151) for controlling the connection assembly to successively connect at least two successive slots (144) to the main line (174).

15 Claims, 3 Drawing Sheets

(56) References Cited

U.S. PATENT DOCUMENTS

| | | | |
|---|---|---|---|
| 7,832,253 B1 * | 11/2010 | Haun | G01N 30/88 422/565 |
| 2003/0000281 A1 * | 1/2003 | Ketler | G01N 33/0006 73/1.06 |
| 2005/0181244 A1 | 8/2005 | Porter et al. | |

* cited by examiner

DEVICE FOR AUTOMATICALLY CALIBRATING AN ANALYZER USED FOR MUD GAS OR FLUID LOGGING, ASSOCIATED ANALYSIS SYSTEM AND DRILLING RIG

The present disclosure concerns a device for automatically calibrating an analyzer used for mud gas or fluid logging.

When drilling an oil well or a well for another effluent (in particular gas, vapour, water), it is known to carry out an analysis of the gaseous compounds contained in the drilling muds emerging from the well. This analysis makes it possible to reconstruct the geological sequence of the formations which are passed through during the drilling operation, and plays a part in determining the possibilities for exploiting the deposits of fluids encountered.

This analysis called "mud gas" or "fluid logging", which is carried out continuously, comprises two main phases. The first phase consists of extracting the gases carried by the mud (for example hydrocarbons, carbon dioxide, hydrogen sulphide, helium and nitrogen). The second phase consists of qualifying and quantifying the gases extracted. In the first phase, mechanically agitated degassers of the aforementioned type (FR-A-2 799 790) are frequently used. The gases extracted from the mud, which are mixed with a carrier gas introduced into the enclosure, are conveyed by suction via the gas extraction pipe to an analyzer which permits the extracted gases to be quantified.

When drilling an oil well, the gases of interest are the C1 to C8 hydrocarbons, the C4 to C5 hydrocarbons branched isomers, aromatic species such as benzene, as well as non-hydrocarbons impurities such as alcohols and ammonia that may result from the drilling fluid. The concentration of each gas typically ranges from 1 to 500,000 ppm. The analyzer must be able to identify and quantify each of those hydrocarbons components, including resolving isomeric species, while tolerating the presence of the non-hydrocarbons.

The industry standard technique for mud gas or fluid logging is gas chromatography. With this technique, gases are separated using a chromatographic column and detected with a thermal conductivity detector, a flame ionization detector or a mass spectrometer.

While these techniques provide good analytical results, the analyzer used during such a technique needs to be carefully calibrated.

The current calibration processes are not only very long but are prone to operator's errors because of the multiple interventions of the operator. As an example, a standard calibration procedure could involve as much as the injection of sixteen different samples containing the hydrocarbons mixtures to be used as calibration points for the analyzer. Such a calibration procedure requires at least sixteen actions of the operator and can last up to six hours.

The disclosure relates to a device for automatically calibrating an analyzer used for mud gas or fluid logging, comprising:
- a cabinet having a plurality of dedicated reception slots, each slot being configured for the insertion of a canister containing a known calibration mixture, the cabinet containing
- a main line to be connected to the analyzer,
- a connection assembly able to selectively connect each reception slot to the main line,
- a control unit for controlling the connection assembly to successively connect at least two successive slots to the main line.

The device according to the disclosure may comprise one or more of the following characteristics, taken in isolation or in any technically possible combinations:
- a plurality of canisters, each canister being configured to be selectively inserted in a slot, each canister containing a known calibration mixture,
- each canister is equipped with an identification device containing information about the calibration mixture contained in the canister, for instance the composition and the concentration of the calibration mixture,
- an identification system connected to the control unit and able to read and send to the control unit the information contained in the identification devices of the canisters,
- the device comprises a presence detection system connected to the control unit, the presence detection system being configured to detect the presence of a canister in a slot,
- the device comprises a pressure measuring system connected to the control unit able to measure the pressure in each canister when the canister is received in a slot,
- the device comprises a warning assembly connected to the control unit, the warning assembly being able to warn an operator in function of data sent by the detection system and/or the identification system and/or the pressure measuring system, for instance:
  if a canister is not located in its dedicated slot, and/or
  if there is no canister in a slot, and/or
  if the pressure in a canister is below a pressure threshold value,
- the device also comprises a purge line able to be connected to a purge system and the control unit is configured to automatically connect the analyzer to the purge system through the main line and the purge line before the first canister connection to the main line and/or between the connection of two canisters containing calibration mixtures with different compositions to the main line,
- the connection assembly for selectively connecting each reception slot to the main line comprises at least one primary valve able to be connected to the main line which can be selectively opened or closed by the control unit,
- the connection assembly selectively connecting each reception slot to the main line comprises at least one secondary valve connected to a canister which can be selectively opened or closed by the control unit.

The disclosure also relates to an analysis system used for mud gas or fluid logging, comprising:
- an analyzer,
- a device as defined above, the main line being connected to the analyzer.

The analysis system related to the disclosure may comprise the following characteristic:
- a purge system, wherein the device comprises a purge line connected to the purge system.

The analysis system related to the disclosure may also comprise the following characteristic:
- the analyzer comprises a gas chromatograph, each canister comprising a gas mixture.

The disclosure further relates to a drilling rig comprising:
- a drilling pipe for the circulation of a drilling mud and/or of a fluid,
- sampling means for sampling the drilling mud and/or fluid coming from the drilling pipe, a gas extractor,
an analysis system as defined above connected to the gas extractor.

The disclosure also relates to a calibration method comprising:
providing an analyzer as defined above;
inserting a plurality of canisters in respective reception slots of the cabinet;
activating the control unit to successively connect each canister inserted in a reception slot to the main line through the connection assembly to deliver the content of the canister to the analyzer.

The disclosure will be better understood on reading the following description, which is given solely by way of example, and is written with reference to the appended drawings, in which.

In everything which follows, the terms "upstream" and "downstream" are understood with respect to the normal direction of circulation of a fluid in a pipe.

A calibration device according to the disclosure is used for example in a drilling rig 11 for an oil production well.

Figure 1:
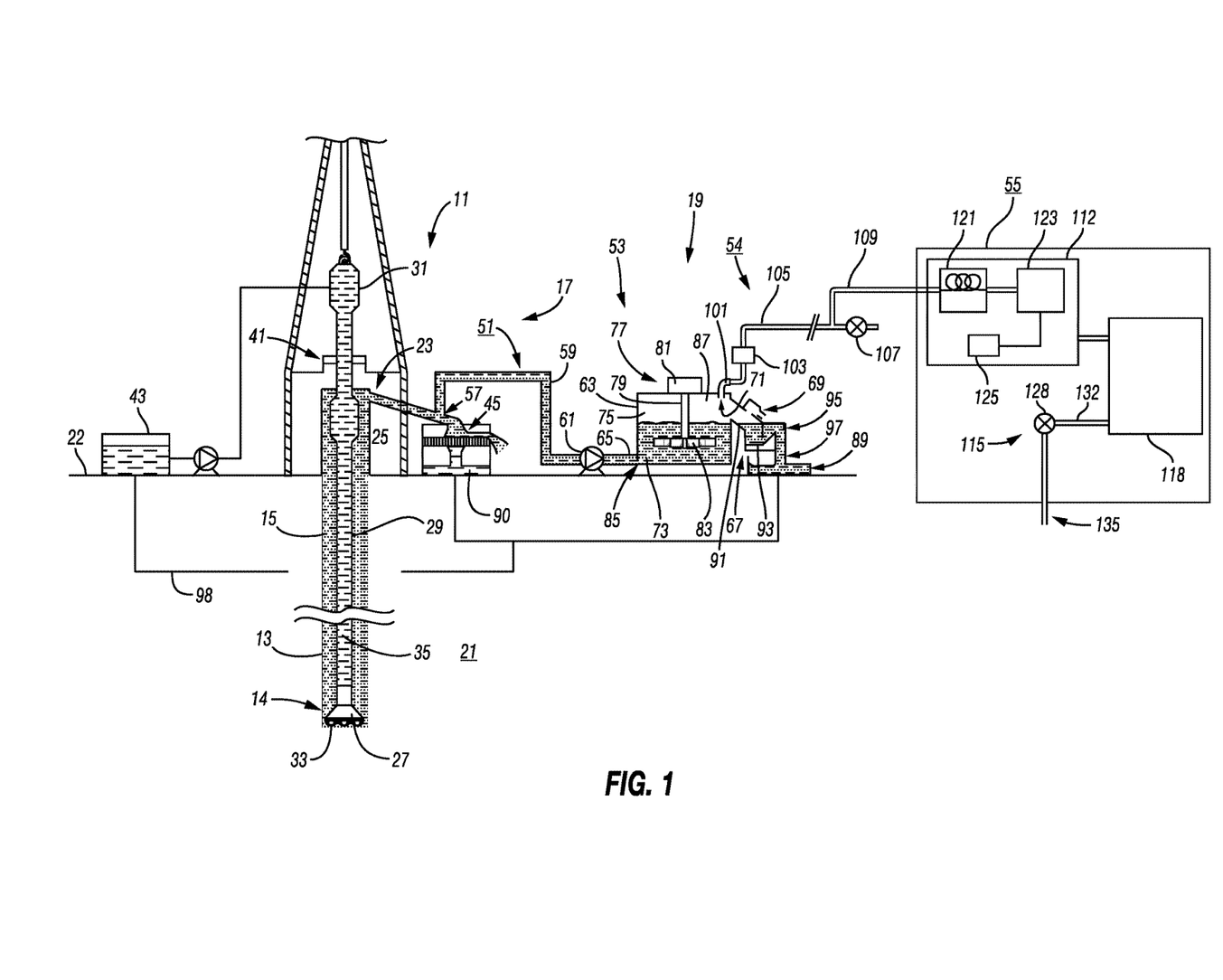
FIG. 1 is a schematic view in vertical section of a drilling rig, provided with an analysis system according to the disclosure.

As illustrated in FIG. 1, this drilling rig 11 comprises a drilling pipe 13 arranged in a cavity 14 bored by a rotary drilling tool 15, a surface installation 17 and an analysis unit 19 according to the disclosure.

The drilling pipe 13 is arranged in the cavity 14 formed in the substratum 21 by the rotary drilling tool 15. This pipe 13 comprises, at the surface 22, a well head 23 provided with a discharge pipe 25.

The drilling tool 15 comprises a drilling head 27, a drill string 29 and a liquid injection head 31.

The drilling head 27 comprises means 33 for drilling through the rocks of the substratum 21. It is mounted on the lower portion of the drill string 29 and is positioned in the bottom of the drilling pipe 13.

The string 29 comprises a set of hollow drilling tubes. These tubes delimit an internal space 35 which makes it possible to bring a liquid from the surface 22 to the drilling head 27. To this end, the liquid injection head 31 is screwed onto the upper portion of the string 29.

The surface installation 17 comprises means 41 for supporting the drilling tool 15 and driving it in rotation, means 43 for injecting the drilling liquid and a shale shaker 45.

The injection means 43 are hydraulically connected to the injection head 31 in order to introduce and circulate a liquid in the inner space 35 of the drill string 29.

The shale shaker 45 collects the liquid laden with drilling residues which emerges from the discharge pipe 25, and separates the liquid from the solid drilling residues.

The analysis unit 19 comprises means 51 for sampling the mud which are tapped into the discharge pipe 25, a gas extractor 53 and a line 54 for transporting the extracted gases which is connected to the extractor. The analysis unit 19 further comprises an analysis system 55 for the extracted gases, into which the transport line 54 opens.

The sampling means 51 comprise a liquid sampling head 57, arranged protruding into the discharge pipe 25, a connecting tube 59 and a peristaltic pump 61, the flow rate of which is adjustable.

In a variant, the sampling means 51 are tapped into a receiving tank for the liquid, into which the discharge pipe 25 opens. In another variant, the sampling means 51 are tapped into a tank of the mud injection means 43.

The extractor 53 comprises an enclosure 63, a pipe 65 for supplying mud into the enclosure 63, a pipe 67 for evacuating the mud from the enclosure 63, an inlet 69 for introducing a carrier gas into the enclosure 63 and an outlet 71 for extracting the extracted gases from the enclosure 63.

The enclosure 63 comprises a hermetic receptacle, the internal volume of which is for example between 0.4 liters and 3 liters. This enclosure 63 comprises a lower portion 73, in which the mud circulates, and an upper portion 75. The enclosure 63 is further provided with agitating means 77, comprising an agitator 79, mounted so as to protrude into the enclosure 63 and driven in rotation by a motor 81 mounted on the upper portion 75 of the enclosure 63. The agitator 79 comprises an agitating mechanism 83 immersed in the mud.

The mud supply pipe 65 extends between the outlet of the peristaltic pump 61 and an entry opening 85, formed in the lower portion 73 or upper portion 75 of the enclosure 63.

This supply pipe 65 may be provided with means for heating the mud (not shown) in order to bring the temperature of this mud to values of between 25 and 150° C., preferably of between 60 and 90° C.

The evacuation pipe 67 extends between an overflow passage 87, formed in the upper portion 75 of the enclosure 63, and a retention basin 89 for receiving the mud evacuated from the device 53.

In a variant, the retention basin 89 is formed by a receiving tank 90 for the liquids extracted from the shale shaker 45.

The evacuation pipe 67 comprises in succession an upstream portion 91 inclined downwards, which is at an angle of approximately 45° to the horizontal, an angled portion 93 forming a siphon, and a substantially vertical downstream portion 95, open at its lower end 97 arranged facing the basin 89, above the level of the liquid contained in the basin 89.

The mud collected in the retention basin 89 and in the tank 90 is recycled to the injection means 43 by a mud recirculation pipe 98.

The introduction inlet 69 opens into the upper portion 75 of the enclosure 63. It is connected to a source (not shown) of a carrier gas such as nitrogen or helium. In a variant, the inlet 69 opens into the atmosphere located around the enclosure 63.

The outlet for evacuating the extracted gases 71 is delimited in an upper portion of the enclosure, in the vicinity of the agitator 79. It comprises a fitting 101 for connection to the transport line 54.

The line 54 is mounted on the fitting 101. The line 54 is capable of continuously sampling a stream of gases extracted from the mud in the upper portion 75 of the enclosure in order to convey this stream to the analysis system 55.

As will be seen below, this gas stream contains hydrocarbons to be analysed, water vapour and impurities such as alcohols and ammonia. The hydrocarbons to be analysed are for example C1 to Cn hydrocarbons, with n being less than or equal to 10, with n being less than or equal to 8.

The transport line 54 connects the enclosure 63 arranged in the vicinity of the well head 23, in the explosive zone, to the analysis system 55, which is arranged spaced apart from the well head 23, in a non-explosive zone, for example in a pressurised cabin. In a variant, the line 54 is very short and the analysis system 55 is placed in the explosive zone in the vicinity of the well head.

The transport line 54 is preferably produced on the basis of a material which is inert towards the gaseous compounds extracted from the mud, such as steel, polyethylene (PE) or PTFE. It has for example a length which varies between 10 cm and 500 m.

The transport line 54 is provided, from upstream to downstream, with a water trap 103, a flow rate controller 105 located in the vicinity of the enclosure 63, a vacuum pump 107 for conveying the extracted gases, and a branch connection 109 for connection to the analysis system 55 opening upstream from the pump 107.

The water trap 103 comprises at least one cold water condensation surface in order to eliminate the water vapour present in the extracted gases substantially by condensation.

The flow rate controller 105 is formed by a tube having a constriction of calibrated cross-section. The controller sets a volume flow rate for the flow of extracted gases which circulates in the line 54. This flow rate is for example of between 300 cm3 per minute and 2000 cm3 per minute, and for instance equal to 500 cm3 per minute.

The pump 107 permits conveying by suction of the gases extracted from the enclosure 63 to the analysis system 55. It is placed in the vicinity of the analysis system 55. It has an inlet connected to the line 54 in parallel to the branch connection 109 and an evacuation outlet which opens into the atmosphere.

The branch connection 109 opens upstream from the inlet into the pump 107. It is capable of sampling approximately 10% of the volume flow rate of extracted gases circulating in the line 54, the rest of the flow of extracted gases circulating through the pump 107 to be evacuated into the atmosphere.

The analysis system 55 comprises an analyzer 112, a purge system 115 and a calibration device 118.

Calibration device 118 may be provided temporarily on-site because it may only be needed at the beginning during the installation of the analyzer 112. The analysis of fluid can also take place without using the calibration device 118.

The analyzer 112 comprises a separation column 121 for the hydrocarbons to be analysed, a detector 123 for successive detection of the hydrocarbons which are separated in the separation column 121, means 125 for qualification and/or quantification of the hydrocarbons to be analysed which are detected by the detector 123 and a memory 126.

The separation column 121 may be a gas chromatograph, for instance a gas-chromatography separation column. This column is for example charged with the aid of a stationary phase in the form of a gel which permits the selective dissolution of the hydrocarbons in the gel in order to retain them selectively (gas-liquid chromatography). In a variant, the column has a solid coating capable of interacting with the hydrocarbons to be analysed in order to retain them selectively according to their affinity with the coating (gas-solid chromatography).

The separation column is capable of eluting in succession the hydrocarbons to be analysed according to the number of atoms which they comprise (from C1 to Cn), starting from a stream injected at the inlet containing all the hydrocarbons to be analysed at a given moment. The hydrocarbons to be analysed emerge from the column 121 at distinct elution times of between 10 s and 100 s.

The detector 123 is for example a flame ionisation detector (FID), or alternatively a thermal conductivity detector (TCD). The detector may possibly be a mass spectrograph, depending on the analysis required on the gases.

The qualification and/or quantification means 125 are capable of qualifying the C1 to Cn hydrocarbons with n being less than or equal to 10, more specifically with n being less than or equal to 8, in order to detect their presence in the gas stream, and of quantifying the relative contents of at least the C1 to C5 hydrocarbons.

The purge system 115 comprises a vacuum pump 128 for extracting the gases contained into the analyzer 112. It has an inlet 132 connected to the calibration device 118 and an evacuation outlet 135 which opens into the atmosphere.

Figure 2:
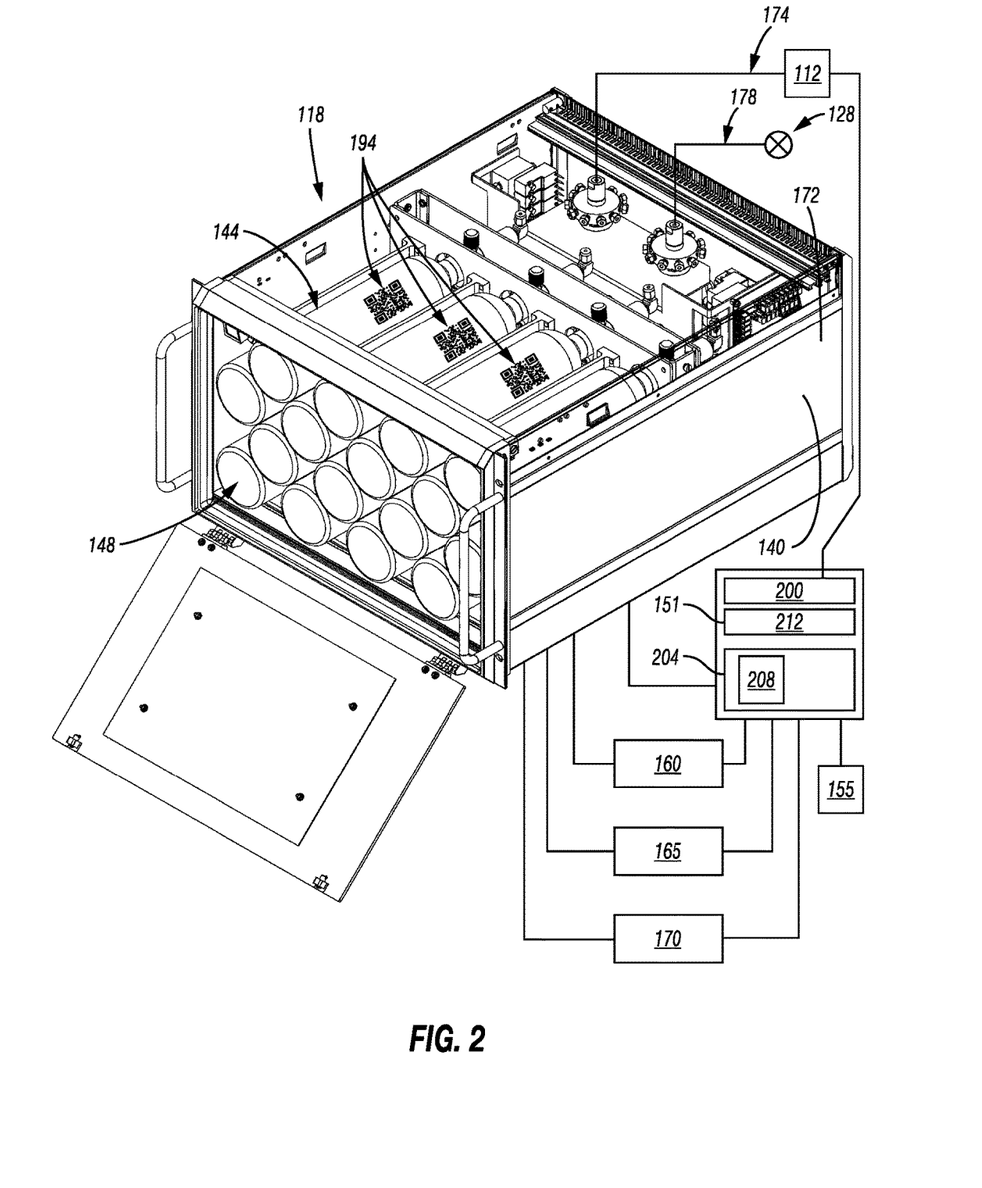
FIG. 2 is a schematic view of a calibration device comprising a cabinet according to the disclosure.
Figure 3:
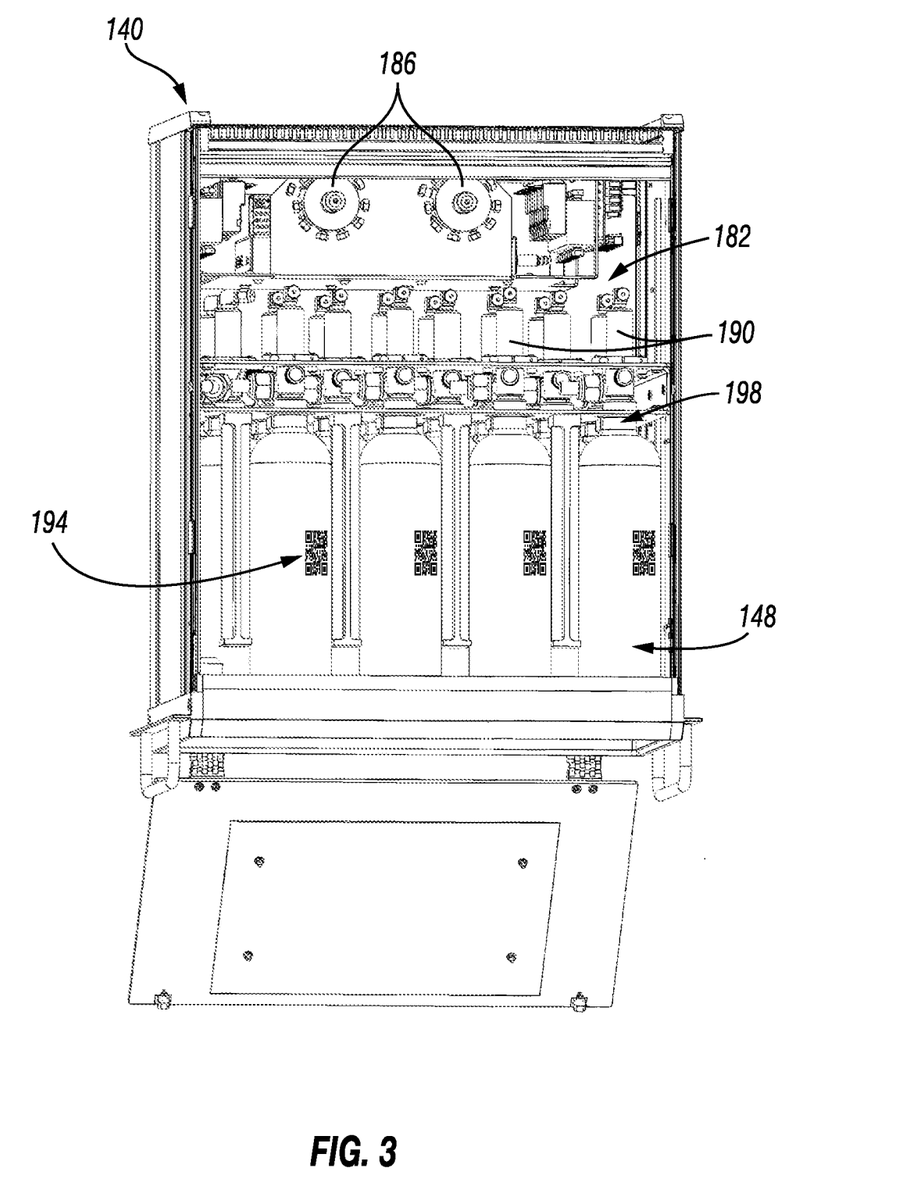
FIG. 3 is a top view of the cabinet of the calibration device of FIG. 2.

As illustrated in FIGS. 2 and 3, the calibration device 118 comprises a cabinet 140 having a plurality of dedicated reception slots 144 being configured for the insertion of canisters and at least one canister 148 provided with a known calibration mixture, being inserted in one of the slot 144.

According to the particular embodiment disclosed here, the cabinet 140 has sixteen slots 148, but a cabinet 140 with more or less than sixteen slots 144 is also suitable.

The calibration device 118 also comprises a control unit 151 configured to be used by an operator for controlling the calibration and a warning assembly 155 connected to the control unit 151.

The calibration device 118 further comprises an identification system 160 configured to identify the mixture contained in each canister 148, a presence detection system 165 configured to detect the presence of a canister 148 in a slot 144 and a pressure measuring system 170 configured to measure the pressure in each canister 148. The calibration device 118 also comprises activation means 172 configured to be used by the operator to start the automatic calibration.

The cabinet 140 comprises a main line 174 to be connected to the analyzer 112, a purge line 178 to be connected to the purge system 115 and a connection assembly 182 configured to selectively connect each reception slot 144 to the main line 174 and/or to the purge line 178. The dimensions of the cabinet 140 are usually between 10 and 60 cm in height, between 30 and 90 cm in length and between 30 and 60 cm in width.

Purge line 178 is used to remove any remaining gas mixture still present in the lines, coming from previous canister 148, when switching to the next canister 148 with a different gas composition.

The connection assembly 182 comprises at least one primary valve 186 which can be selectively opened or closed by the control unit 151. According to the disclosure, the connection assembly 182 comprises two primary valves 186 to be connected to the main line 174 and/or to the purge line 178. The main line 174 and the purge line 178 are also connected thanks to the primary valves 186.

The primary valves 186 are for example rotating valves.

The connection assembly 182 also comprises at least one secondary valve 190 to be connected to one of the canister 148 and to one of the primary valve 186. According to the disclosure, the connection assembly 182 comprises the same number of secondary valves 190 than the number of slots 144. In the particular example disclosed here, the connection assembly 182 comprises therefore sixteen secondary valves 190. The secondary valves 190 are for example electrovalves.

This configuration of the connection assembly 182 is of course one among others as the connection assembly 182 may not comprise primary valves 186 and secondary valves 190, but only primary valves 186 (with a minimum of one primary valve 186), each primary valve 186 being able to directly connect the outlet of each canister 148 to the main line 174. When it comprises primary valves 186 and secondary valves 190, the number of primary valves 186 may be different from two.

Each canister 148 comprises a bottle for example made of metal. The internal volume of the bottle is preferably lower than 5 liters at atmospheric pressure (1013 hPa) and ambient temperature (20° C.), as a little amount of gas is enough to perform calibration. The calibration device is then compact.

Each canister 148 contains a known calibration mixture, for example a mixture of some of the C1 to C8 hydrocarbons. The calibration device 118 comprises the same number of canisters 148 than the number of reception slots 144.

Each canister 148 is provided with an identification device 194, such as a label, for the identification of the canister 148. The identification devices 194 are specific to one calibration mixture and therefore specific to one canister 148. An identification device 194 comprises a reference number specific to one canister 148 and information about the composition and the concentration of the calibrating mixture contained in this canister 148. The identification devices 194 are for example QR barcode or RFID label which can be read by the identification system 160.

The canister 148 also comprises a pressure regulator 198 used to carry the gas stored in the canister 148 outside the canister 148. The pressure regulator 198 is able to decrease the pressure of the gas mixture contained in the bottle to deliver the gas mixture to the connection assembly 182.

Each canister 148 is configured to be selectively inserted in a reception slot 144 of the cabinet 140.

The control unit 151 comprises a processor 200, a memory 204, a software application 208 stored in the memory 204 and that can be executed thanks to the processor and a man-machine interface 212. The software application 208 is configured to be executed by the processor 200.

The software application 208 comprises a first module configured to collect the data from the identification system 160, the presence detection system 165 and the pressure measuring system 170.

The software application further comprises a second module configured to transmit some of the data collected by the first module to the analyzer 112 so that the analyzer 112 can properly set up the calibration process and the calibration calculations.

It also comprises a third module configured to analyse the data collected by the first module and to activate the warning assembly 155 if predetermined conditions are met, such as if the analysed data indicate that a canister 148 is not located in its dedicated slot 144, and/or if there is no canister 148 in a slot 144 and/or if the pressure in a canister 148 is below a pressure threshold value.

The pressure threshold value can be chosen by the operator using the man-machine interface 212. For example, the pressure threshold value is 50 psi. The third module is also able to stop the warning assembly 155.

The software application also comprises a fourth module configured to control the connection assembly 182 in order to process the calibration. The fourth module is therefore able to command the opening or the closing of the primary valves 186 and of the secondary valves 190. The fourth module is also able to choose predetermined canisters 148 to be used for the calibration and to start the automatic calibration. The fourth module is also able to automatically connect the analyzer 112 to the purge system 115 through the main line 174 and the purge line 178 before the first canister connection to the main line 174 and/or between the connection of two canisters 148 containing calibration mixtures with different compositions to the main line 174.

The man-machine interface 212 is for example a touch-screen or a keyboard.

The warning assembly 155 is controlled by the control unit 151. The warning assembly 155 is able to generate at least one alarm. The warning assembly 155 is able to generate three different alarms: the first one being configured to warn the operator if a canister 148 is not located in its dedicated slot, the second one being configured to warn the operator if there is no canister 148 in a slot 144 and the third one being configured to warn the operator if the pressure in a canister 148 is below the pressure threshold value. The warning assembly 155 is for example a panel of LEDS, each alarm being associated with a specific colour of LED, and/or an alarm ring.

Of course, only one or two of these conditions may be checked and trigger warnings. Other conditions may also trigger additional warnings. There may be no dedicated slot for each canister for instance, the device being able to perform the calibration process with a canister containing a known calibration mixture inserted in any slot.

The identification system 160 is an electronic device configured to read the identification device 194 on each canister 148 and to send the data contained in each identification device 194 to the control unit 151. The identification system 160 is electronically connected to the control unit 151. The identification system 160 is for example an optical barcode reader adapted to be manipulated by an operator.

The presence detection system 165 is an electronic device configured to detect the presence of a canister 148 in a slot 144 and to determine whether each canister 148 is properly inserted in its dedicated slot 144.

The presence detection system 165 is electronically connected to the control unit 151. The presence detection system 165 is able to send information about the presence of a canister 148 in a slot 144, about the presence of a canister 148 not properly inserted in its dedicated slot 144 and about the absence of canister 148 in a slot 144 to the central unit 151. The presence detection 165 is also configured to count the number of canisters 148 in the cabinet 140 and to send this information to the central unit 151.

The pressure measuring system 170 is an electronic device connected to the control unit 151 and configured to measure the pressure in each canister 148. It is also configured to send the measured pressure data to the control unit 151. The pressure measuring system 170 is for example a vacuometer.

The activation means 172 are for example a button that can be pressed by an operator to start the automatic calibration.

The calibration method according to the disclosure will now be described as an example, with reference to FIG. 1 and FIG. 2.

During an initial step, the operator inserts the selected canisters 148 in their dedicated slots 144.

Then, the identification system 160 reads the identification device 194 on each canister 148 and sends the information contained in the identification device 194 to the central unit 151. The central unit 151 transfers this data to the analyzer 112. The presence detection system 165 counts the number of canisters 148 in the cabinet 140 and sends this information to the central unit 151.

When all desired canisters 148 are installed, the operator starts the automatic calibration by using the activation means 172.

Before the first selected gas canister injection, the central unit 151 controls the connection of the analyzer 112 to the purge system 115 through the opening or the closing of the primary valves 186, with all secondary valves 190 closed. Purge is performed for some seconds, then the primary valves 186 move back to their previous position.

Thereafter, the central unit 151 orders the start of the calibration with a chosen canister 148.

The presence detection system 165 detects the presence of the canister 148 in a slot 144 and sends this information to the central unit 151. When the canister 148 is not properly inserted in its dedicated slot 144, the presence detection system 165 sends this information to the central unit 151. If there is no canister in the considered slot 144 or if the canister 148 is not properly inserted in the slot 144, the central unit 151 activates the warning assembly 155.

In parallel, the pressure measuring system 170 measures the pressure in the canister 148 and send the measured pressure data to the control unit 151. If the pressure in the canister 148 is below the pressure threshold value, the central unit 151 activates the warning assembly 155.

When the operator wants to stop the warning assembly 155, he can either change the canister 148 or send a stop order to the control unit 151 using the man-machine interface 212.

When the warning assembly 155 is activated, the calibration performed with the chosen canister 148 is stopped and the calibration is carried on with the following canister 148.

If the canister 148 is properly placed and connected and if it contains the appropriate mixture of gases at the relevant pressure, the control unit 151 controls the primary valve 186 of the connection assembly 182 to selectively connect the canister 148 to the main line 174 through the connection assembly 182 to deliver the content of the canister 148 to the analyzer 112.

The analyzer 112 is hence connected to a single canister 148 at a time, the canister 148 being located in its dedicated slot 144, and having been tested for content identification and pressure level. The reliability of the operation is therefore increased.

Then, the analyzer 112 performs the analysis of the mixtures of gases injected and determines the peak area associated to this mixture of gases. Peak areas corresponding to the different mixtures of gases injected are stored in the analyzer 112 to be used later as calibrations points for unknown mixtures of gases in order to allow the determination of unknown gases.

After the injection of the first canister 148, the control unit 151 repeats the same operation for the others canisters 148.

Between the injections of canisters containing calibration mixtures with different compositions, the central unit 151 controls the primary valves 186 to connect the analyzer 112 to the purge system 115. The primary valves 186 connect the main line 174 to the purge line 178. Purge is performed for some seconds, then the primary valves 186 move back to their previous position.

Each canister 148 inserted in a reception slot 144 is then subsequently connected selectively to the main line 174 through the connection assembly 182 to deliver the content of the canister 148 to the analyzer 112.

Hence, the calibration process is automatically performed with injection runs from identical canister compositions going from low to high concentration levels to not only reduce purging time but to eliminate as well as possible mixing of injected concentrations. A longer purge is automatically performed when gas mixture composition is changed.

When all selected canisters 148 have been injected, the calibration process is stopped.

Thanks to the calibration device 118, the calibration process is almost fully automated to the extent that it only requires the intervention of the operator to insert the canisters 148 in their dedicated slot 144 and to activate the activation means 172. The operator can control the calibration process using the man-machine interface 212 of the central unit 151 and is informed when the calibration is not possible thanks to the warning assembly 155. Hence, such a calibration device 118 reduces the probability of operator's errors.

Moreover, the calibration processed by the calibration device 118 is not only reliable but also rather fast as a calibration involving sixteen different canisters 148 can be performed in two hours compared to the six hours of the current calibration device.

Finally, thanks to the small size of the cabinet 140, the calibration device 118 is suitable to be used to calibrate an analyzer used during mud gas or fluid logging, in the vicinity of an oil and gas well, for example at a distance lower than 500 meters from the oil well.

The invention claimed is:

1. A device for automatically calibrating an analyzer used for mud gas or fluid logging, comprising:
   a cabinet having a plurality of dedicated reception slots, the cabinet containing:
   a main line to be connected to the analyzer,
   a connection assembly able to connect each canister disposed in the reception slot to the main line, wherein the connection assembly is able to selectively provide fluid communication with the main line,
   a plurality of canisters, each canister being configured to be inserted in a slot, each canister containing a known calibration mixture, wherein each canister is equipped with an identification device containing information about the calibration mixture contained in the canister,
   a control unit for controlling the connection assembly to successively connect at least two canisters to the main line,
   an identification system connected to the control unit and able to read and send to the control unit the information contained in the identification devices of the canisters.

2. The device according to claim 1, wherein the device comprises a presence detection system connected to the control unit, the presence detection system being configured to detect the presence of a canister in a slot.

3. The device according to claim 2, wherein the device comprises a warning assembly connected to the control unit, the warning assembly being able to warn an operator in function of data sent by the detection system if there is no canister in a slot.

4. The device according to claim 1, wherein the device comprises a pressure measuring system connected to the control unit able to measure the pressure in each canister when the canister is received in a slot.

5. The device according to claim 4, wherein the device comprises a warning assembly connected to the control unit, the warning assembly being able to warn an operator based on data sent by the pressure measuring system, if the pressure in a canister is below a pressure threshold value.

6. The device according to claim 1, wherein the device also comprises a purge line able to be connected to a purge system and wherein the control unit is configured to automatically connect the analyzer to the purge system through the main line and the purge line before the first canister connection to the main line and/or between the connection of two canisters containing calibration mixtures with different compositions to the main line.

7. The device according to claim 1, wherein the connection assembly for selectively connecting each canister to the main line comprises at least one primary valve able to be connected to the main line which can be selectively opened or closed by the control unit.

8. A device according to claim 1, wherein the connection assembly for selectively connecting each canister to the main line comprises at least one secondary valve connected to a canister which can be selectively opened or closed by the control unit.

9. An analysis system used for mud gas or fluid logging, comprising:
  an analyzer,
  a device according to claim 1, the main line being connected to the analyzer.

10. The analysis system according to claim 9, comprising a purge system, wherein the device comprises a purge line connected to the purge system.

11. The analysis system according to claim 9 wherein the analyzer comprises a gas chromatograph, each canister comprising a gas mixture.

12. A drilling rig comprising:
  a drilling pipe for the circulation of a drilling mud and/or of a fluid,
  sampling means for sampling the drilling mud and/or the fluid coming from the drilling pipe,
  a gas extractor for extracting gas from the sampled drilling mud and/or the fluid,
  an analysis system according to claim 9 connected to the gas extractor for analyzing the extracted gas.

13. A calibration method comprising:
  providing an analyzer according to claim 9;
  inserting a plurality of canisters in respective reception slots of the cabinet;
  activating the control unit to successively provide fluid communication between each canister inserted in a reception slot and the main line through the connection assembly to deliver the content of said canister to the analyzer.

14. The device according to claim 1, wherein the information includes the composition and the concentration of the calibration mixture.

15. The device according to claim 1, wherein the device comprises a warning assembly connected to the control unit, the warning assembly being able to warn an operator in function of data sent by the identification system if a canister is not located in a predetermined slot.

* * * * *